(12) United States Patent
Sardeshmukh et al.

(10) Patent No.: US 12,201,660 B2
(45) Date of Patent: Jan. 21, 2025

(54) HERBO-MINERAL COMPOSITION FOR ALLEVIATING ADVERSE EFFECTS OF CHEMOTHERAPY IN CANCER PATIENTS

(71) Applicant: Sadanand Prabhakar Sardeshmukh, Pune (IN)

(72) Inventors: Sadanand Prabhakar Sardeshmukh, Pune (IN); Vineeta Vasant Deshmukh, Pune (IN)

(73) Assignee: Sadanand Sardeshmukh, Pune (IN)

( * ) Notice: Subject to any disclaimer, the term of this patent is extended or adjusted under 35 U.S.C. 154(b) by 706 days.

(21) Appl. No.: 17/609,601

(22) PCT Filed: Feb. 12, 2020

(86) PCT No.: PCT/IB2020/051116
§ 371 (c)(1),
(2) Date: Nov. 8, 2021

(87) PCT Pub. No.: WO2020/225610
PCT Pub. Date: Nov. 12, 2020

(65) Prior Publication Data
US 2022/0202888 A1 Jun. 30, 2022

(30) Foreign Application Priority Data
May 7, 2019 (IN) .............................. 201921018273

(51) Int. Cl.
*A61K 36/24* (2006.01)
*A61K 9/20* (2006.01)
(Continued)

(52) U.S. Cl.
CPC .............. *A61K 36/24* (2013.01); *A61K 9/205* (2013.01); *A61K 36/59* (2013.01); *A61K 36/62* (2013.01); *A61K 36/899* (2013.01); *A61P 1/08* (2018.01)

(58) Field of Classification Search
None
See application file for complete search history.

(56) References Cited

U.S. PATENT DOCUMENTS

2018/0318374 A1  11/2018  Shetty

OTHER PUBLICATIONS

Anjali A. Deshpande, Assessment of Effect of CG4 (An Ayurvedic Formulation) in The Management of Side Effects of Chemotherapy in Breast Cancer, (2016) (Ph. D. dissertation, Tilak Maharashtra Vidyapeeth, Pune). (Year: 2016).*

(Continued)

*Primary Examiner* — Dominic Lazaro
(74) *Attorney, Agent, or Firm* — The Roy Gross Law Firm, LLC; Roy Gross

(57) ABSTRACT

The present disclosure relates to a herbo-mineral kit for alleviating adverse effects of chemotherapy resulting into improved quality of life of patients. The herbo-mineral kit comprises a first container containing Padmakadi Ghrut (PDG) in a thick, viscous form; a second container containing Mouktikyukta Kamdudha Vati (MKD) in a solid dosage form; a third container containing Praval Pishti Vati (PPV) in a solid dosage form; and a fourth container containing Ananta vati in a solid dosage form. The herbo-mineral kit of the present disclosure can be used for alleviating adverse effects of chemotherapy such as nausea, vomiting, constipation, diarrhea, stomatitis, and skin discoloration in cancer treatment. Use of the herbo-mineral kit of the present disclosure may prove to be beneficial in all types of cancers and diseases for which chemotherapy is treatment of choice.

12 Claims, 6 Drawing Sheets

(51) Int. Cl.
  *A61K 36/59* (2006.01)
  *A61K 36/62* (2006.01)
  *A61K 36/899* (2006.01)
  *A61P 1/08* (2006.01)

(56) References Cited

OTHER PUBLICATIONS

Gujar, Shweta R., Role of RG4 an Ayurvedic formulation 1-8 in the management of side effects of radiotherapy of oral cavity cancers, (2015) (Ph. D. dissertation, Tilak Maharashtra Vidyapeeth, Pune). (Year: 2015).*

Singh, J., Praval Pishti (Coral Calcium) Benefits & Side Effects, Mar. 15, 2015; accessed Sep. 29, 2024 at https://www.ayurtimes.com/praval-pishti-coral-calcium-benefits-side-effects/. (Year: 2015).*

Deshpande, A., "Assessment of Effect of CG4 (An Ayurvedic Formulation) in The Management of Side Effects of Chemotherapy in Breast Cancer", A thesis submitted to Tilak Maharashtra Vidyapeeth, Pune For the Degree of Doctor of Philosophy (Ph. D.) Month & Year: Dec. 2016.

Gujar, SR, "Role of RG4 an Ayurvedic formulation in the management of side effects of radiotherapy of oral cavity cancers", A thesis submitted to Tilak Maharashtra Vidyapeeth, Pune For the Degree of Doctor of Philosophy (Ph. D.), Month & Year. Sep. 2015.

Kumar, M.S. et al., Kamadugha Rasa An Effective Ayurvedic Formulation For Peptic Ulcer: A Review, Global J Res. Med. Plants & Indigen. Med., (2014), vol. 3 (1) : 24-32. Retrieved Nov. 8, 2021 from: https://www.researchgate.net/publication/282877295_KAMADUGHA_RASA_AN_EFFECTIVE_AYURVEDIC_FORMULATION_FOR_PEPTIC_ULCER_A_Review.

Dr. Jagdev Singh, Praval Pishti (Coral Calcium) Benefits & Side Effects, Published: Mar. 14, 2015. Retrieved from: https://www.ayurtimes.com.

TKDL database: Abstract Id: AK15/197, Title: Pravala Pancamrita Rasah, Bibliography: Rasm·· tam , Knowledge Known Since: 50 years.

TKDL database: Abstract Id: BS05/192, Title: Kalyana Grutham, Bibliography: Agasthiyar 2000; vol. III, Knowledge Known Since: I000years.

TKDL database: Abstract Id: RG12/984, Title: Gulkanda( Pravala Misirita ), Bibliography: yurveda Srasagraha , Knowledge Known Since: 50 years.

PCT International Search Report for International Application No. PCT/IB2020/051116, mailed Jul. 29, 2020, 3pp.

PCT Written Opinion for International Application No. PCT/IB2020/051116, mailed Jul. 29, 2020, 6pp.

* cited by examiner

HERBO-MINERAL COMPOSITION FOR ALLEVIATING ADVERSE EFFECTS OF CHEMOTHERAPY IN CANCER PATIENTS

This application is a National Phase of PCT Patent Application No. PCT/IB2020/051116 having an International filing date of Feb. 12, 2019, which claims the benefit of priority of Indian patent application No. 201921018273, filed May 7, 2019, the contents of which are all incorporated herein by reference in their entirety.

FIELD

The present disclosure relates to a herbo-mineral kit. Particularly, the present disclosure relates to a herbo-mineral kit for alleviating adverse effects of chemotherapy.

Abbreviations

WBC: White blood cells.
SGOT: Serum glutamic oxaloacetic transaminase.
SGPT: Serum glutamic pyruvic transaminase.
RSR: Respective survival rate
QoL: Quality of Life
QLQ C 30: Quality of Life Questionnaire

Definitions

As used in the present disclosure, the following terms are generally intended to have the meaning as set forth below, except to the extent that the context in which they are used indicate otherwise.

Padmak: The term "Padmak" refers to "Lotus (*Nelumbo nucifera*)".

Durva: The term Durva refers to "Burmuda grass (*Cynodon dactylon*)".

Ananta: The term Ananta refers to "Swallow root (*Decalepis hamiltonii*) or *Hemidesmus indicus* or *Cryptolepis buchnani* or *Ichnocarpus frutescens*.".

Ghrut: The term "Ghrut" refers to "clarified butter" or "Ghee" especially cow's Ghee.

Shankha bhasma: The "Shankha bhasma" refers to "incinerated Conch shell". The term "Shankha bhasma" referred in the present disclosure is not the same, as used in Ayurveda.

Shouktik bhasma: The term "Shouktik bhasma" refers to "incinerated pearl shell". The term "Shouktik bhasma" referred in the present disclosure is not the same, as used in Ayurveda.

Kapardika bhasma: The "Kapardika Bhasma" refers to "incinerated Cowries". The term "Kapardika Bhasma" referred in the present disclosure is not the same, as used in Ayurveda.

Pravala bhasma: The "Pravala Bhasma" refers to "incinerated coral". The term "Pravala bhasma" referred in the present disclosure is not the same, as used in Ayurveda.

Mouktik bhasma: The term "Mouktik bhasma" refers to "incinerated pearl," natural or cultured. The term "Mouktik bhasma" referred in the present disclosure is not the same, as used in Ayurveda.

Shuddha Gairik: The "Gairik" is a natural clay earth pigment which is a mixture of ferric oxide and varying amounts of clay and sand. "Shuddha Gairik" refers to "processed Gairik", prepared by roasting Gairik in cow ghee. The term "Shuddha Gairik" referred in the present disclosure is not the same, as used in Ayurveda.

Guduchi Sattva: The term "Guduchi Sattva" refers to extract comprising mainly starch of *Tinospora cordifolia/sinensis/glabra/crispa* prepared by alcoholic, hydro-alcoholic or aqueous extraction method. The term "Guduchi Sattva" referred in the present disclosure is not the same, as used in Ayurveda.

Praval Pishti: The term "Praval Pishti" refers to powdered coral triturated with rose water. The term "Praval Pishti" referred in the present disclosure is not the same, as used in Ayurveda.

Vati: The term "Vati" refers to a method of medicine preparation in which herbs, minerals, and metallic compounds are compressed into tablet form.

Trituration: The term "trituration" refers to either reducing the particle size of a substance or production of a homogeneous material by mixing component materials thoroughly or wet grinding any material with a liquid media like fresh juice or decoction etc.

Karnofsky score: The term "Karnofsky score" refers to the Karnofsky Performance Scale Index allows patients to be classified as to their functional impairment Symptom score: Symptom score of QLQ is indicative of symptomatology; hence decrease in symptom score represents both decrease in disease related symptoms and adverse effects of conventional treatment.

Function score: Functional score of QLQ signifies status of routine physical activities. Increase in functional scores represents improvement in QoL.

Global score: Global score of QLQ represents overall well-being of a patient. Increase in global scores represents improvement in QoL.

BACKGROUND

The background information herein below relates to the present disclosure but is not necessarily prior art.

By definition, the treatment of disease by means of chemicals that have a specific toxic effect upon the disease producing microorganisms (antibiotics) or that destroy cancerous tissue (anticancer therapy) is included under chemotherapy. Chemotherapy is known to produce favorable results; however, it also produces generalized toxic effects such as nausea, vomiting, diarrhoea, fever, fatigue, skin discoloration, rigors and the like.

Among the various causes of deaths, cancer ranks next to cardiovascular diseases worldwide. It is expected that deaths due to cancer diseases will increase rapidly over the next 2 decades. The existing modalities of treatment of cancer include surgery, radiotherapy and chemotherapy.

Chemotherapy is used to reduce the primary tumour load as well as distant metastasis. However, chemotherapy induces adverse side effects. The toxicity is mainly caused by the inability of chemotherapeutic drugs to distinguish between dividing cancer cells and dividing normal cells. The adverse side effects are nausea, vomiting, loss of appetite, diarrhea, constipation, weakness, alopecia (loss of hair) and neurological problems. These adverse effects interfere with continuation of therapy and results into poor quality of life of patients.

Efforts were made to overcome these side effects by using alternative or adjunct therapies. These therapies did not show effective reduction in the side effects.

Therefore, there is felt a need to provide a specific combination of herbal and mineral ingredients, in the form of a kit, that mitigates the foretasted drawbacks.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a herbo-mineral kit.

Still another object of the present disclosure is to provide a herbo-mineral kit for alleviating adverse effects of chemotherapy.

Other objects and advantages of the present disclosure will be more apparent from the following description, which is not intended to limit the scope of the present disclosure.

SUMMARY

The present disclosure provides a herbo-mineral kit comprising a first container containing Padmakadi Ghrut (PDG) in a thick, viscous form; a second container containing Mouktikyukta Kamdudha Vati (MKD) in a solid dosage form; a third container containing Praval Pishti Vati (PPV) in a solid dosage form, and a fourth container containing Ananta vati in a solid dosage form.

Padmakadi Ghrut (PDG) comprises an extract of petals and stalks of Padmak, an extract of whole Durva plant, decoction of roots of Ananta, and Ghee obtained from cow's milk in an amount ranging from 90 wt % to 98 wt % of the total weight of the PDG, wherein the extract of Padmak, the extract of Durva and the decoction of Ananta are independently obtained by using at least one solvent selected from the group consisting of alcohol, water, and a mixture thereof. The amount of the combined extracts of Padmak, Durva and Ananta is in the range of 2 wt % to 10 wt % of the total weight of the PDG. The Padmakadi Ghrut (PDG) is in a thick, viscous form.

The Mouktikyukta Kamdudha Vati (MKD) comprises Mouktik bhasma in an amount ranging from 10 wt % to 14 wt % of the total weight of the MKD, Shankha bhasma in an amount ranging from 10 wt % to 14 wt % of the total weight of the MKD, Shouktik bhasma in an amount ranging from 10 wt % to 14 wt % of the total weight of the MKD, Kapardik bhasma in an amount ranging from 10 wt % to 14 wt % of the total weight of the MKD, Praval bhasma in an amount ranging from 10 wt % to 14 wt % of the total weight of the MKD, Guduchi sattva in an amount ranging from 10 wt % to 14 wt % of the total weight of the MKD, Shuddha Gairik in an amount ranging from 10 wt % to 14 wt % of the total weight of the MKD, wherein Gairik is processed in ghee obtained from cow's milk, and at least one excipient in an amount ranging from 10 wt % to 25 wt % of the total weight of the MKD.

Praval Pishti Vati (PPV) comprises coral powder passed through mesh number 200 having particle size in the range of 50 microns to 75 triturated in rose water and dried, wherein the total amount of dried triturated coral powder is in the range of 75 wt % to 92 wt % of the total weight of the PPV, and at least one excipient in an amount ranging from 8 wt % to 25 wt % of the total weight of the Praval Pishti Vati.

The Ananta Vati comprises powder obtained from dried roots of Ananta in an amount ranging from 75 wt % to 92 wt % of the total weight of the Ananta Vati, and at least one excipient in an amount ranging from 8 wt % to 25 wt % of the total weight of the Ananta Vati. The particle size of the dried root powder is in the range of 150 microns to 180 microns.

The excipient is a binder. The binder is at least one selected from the group consisting of gum acacia, guar gum, xanthan gum or any other edible gum.

The compositions of MKD, PPV, and Ananta Vati are prepared in a solid dosage form selected from the group consisting of tablet, pill, and capsule.

BRIEF DESCRIPTION OF THE ACCOMPANYING DRAWING

The present disclosure will now be described with the help of the accompanying drawing, in which.

DETAILED DESCRIPTION

Figure 1:
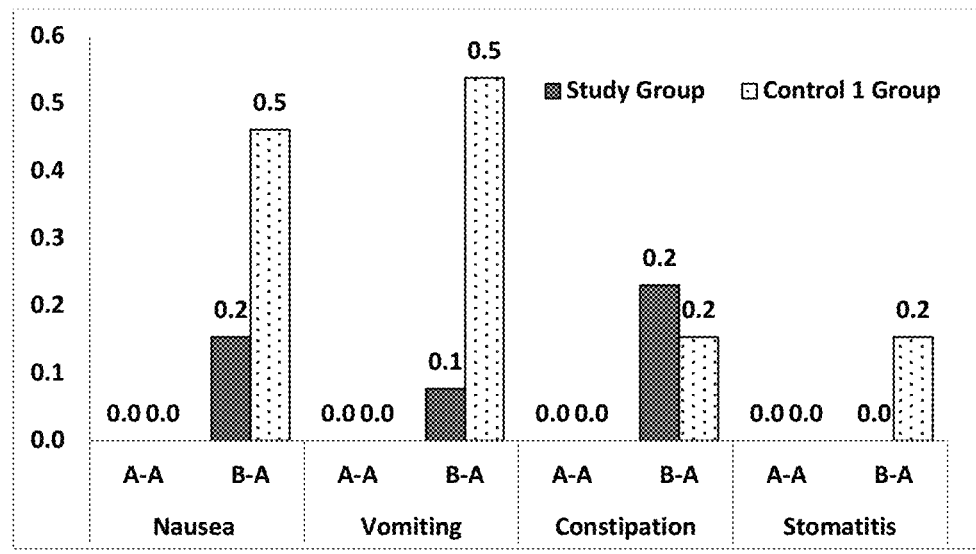
FIG. 1 depicts a graphical representation of the effect of the herbo-mineral kit treatment on chemotherapy induced nausea, vomiting, constipation and stomatitis in study and control 1 group patients.

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The incidences of cancer are increasing worldwide. Chemotherapy is used to reduce the primary tumour load as well as recurrence and metastasis. Although, chemotherapy is an unavoidable line of treatment for cancer, the adverse effects of chemotherapy frequently interfere with continuation of chemotherapy. The adverse effects are due to generation of oxidative stress, inability to control inflammation, reduction in immune response and functional impairment in tissues. These destructive effects result in impairment of quality of life of patients.

Therefore, the present disclosure provides a selected combination of compositions, in the form of a kit that mitigates the foretasted drawbacks.

In an aspect of the present disclosure, there is provided a herbo-mineral kit for alleviating adverse effects of chemotherapy, and for improving quality of life. The herbo-mineral kit comprises: a first container containing Padmakadi Ghrut (PDG) in a thick, viscous form; a second container containing Mouktikyukta Kamdudha Vati (MKD) in a solid dosage form; a third container containing Praval Pishti Vati (PPV) in a solid dosage form; and a fourth container containing Ananta vati in a solid dosage form.

Padmakadi Ghrut (PDG) comprises an extract of petals and stalks of Padmak, an extract of whole Durva plant, a decoction of roots of Ananta, and Ghee obtained from cow's milk in an amount ranging from 90 wt % to 98 wt % of the total weight of the PDG. The extract of Padmak, the extract of Durva and the decoction of Ananta are independently obtained by using at least one solvent selected from the group consisting of alcohol, water, and a mixture thereof. The amount of the combined extracts of Padmak, Durva and Ananta is in the range of 2 wt % to 10 wt % of the total weight of the PDG. The Padmakadi Ghrut is in a thick viscous form.

In an embodiment, the extracts of petals and stalks of Padmak, whole Durva plant, and roots of Ananta are mixed with predetermined amount of ghee obtained from cow's milk. The mixture is heated uniformly with stirring to evaporate the water completely. The complete removal of water is confirmed by the wick test. The active ingredients of the extracts are dispersed in the ghee to obtain mixture. The mixture is filtered through muslin cloth to obtain PDG. The expiry of PDG is 2 years.

Padmak is a common name for *Nelumbo nucifera*. *Nelumbo nucifera* is of the family Nymphaceae and the genus *Nelumbo*. *Nelumbo nucifera* is found in India, Sri Lanka, virtually all of Southeast Asia, New Guinea and northern and eastern Australia. *Nelumbo nucifera* is obtained from Bharatiya Sanskriti Darshan Trust (BSDT), Wagholi, Pune.

Durva is a common name for *Cynodon dactylon* belongs to the family Poaceae. *Cynodon dactylon* is originated in the Middle East. It is also found in India, Bermuda, and North America. *Cynodon dactylon* is obtained from Bharatiya Sanskriti Darshan Trust (BSDT), Wagholi, Pune.

Ananta is a common name for *Decalepis hamiltonii*. *Decalepis hamiltonii* belongs to the family Apocynaceae. It is found in South India. *Decalepis hamiltonii* is obtained from Bharatiya Sanskriti Darshan Trust (BSDT), Wagholi, Pune.

Ananta is roots of *Decalepis hamiltonii* (Swallow roots) or *Hemidesmus indicus* or *Cryptolepis buchnani* or *Ichnocarpus frutescens*. In an embodiment, Ananta is *Decalepis hamiltonii* (Swallow roots). *Decalepis hamiltonii* (Swallow roots) is used due to commercial availability, however, it is asserted that *Hemidesmus indicus* or *Cryptolepis buchnani* or *Ichnocarpus frutescens* will equally be effective, alone or in combination with each other.

Cow Ghee or "clarified butter" is obtained from Bharatiya Sanskriti Darshan Trust (BSDT), Wagholi, Pune. PDG is administered at a dose of 8 gm to 12 gm per day by oral administration.

In an embodiment of the present disclosure, the excipient is a binder. The binder is selected from the group consisting of gum acacia, guar gum, and xanthan gum. In an embodiment of the present disclosure, the binder is gum acacia.

The Mouktikyukta Kamdudha Vati (MKD) comprises Mouktik bhasma in an amount ranging from 10 wt % to 14 wt % of the total weight of the MKD, Shankha bhasma in an amount ranging from 10 wt % to 14 wt % of the total weight of the MKD, Shouktik bhasma in an amount ranging from 10 wt % to 14 wt % of the total weight of the MKD, Kapardik bhasma in an amount ranging from 10 wt % to 14 wt % of the total weight of the MKD, Praval bhasma in an amount ranging from 10 wt % to 14 wt % of the total weight of the MKD, Guduchi sattva in an amount ranging from 10 wt % to 14 wt % of the total weight of the MKD, Shudhha Gairik in an amount ranging from 10 wt % to 14 wt % of the total weight of the MKD, wherein the Shudhha Gairik is processed in ghee obtained from cow's milk, and at least one excipient in an amount ranging from 10 wt % to 25 wt % of the total weight of the MKD.

The quantities below 10 wt % the Mouktik Bhasma will be sub-therapeutic and in quantities greater than 14 wt %, there will be an overload of the Bhasma which will be excreted. Similarly, the lower and upper weight percentages of the other ingredients i.e. Praval Bhasma, Shankha Bhasma, Shouktik Bhasma, Kapardik Bhasma, Shudhha Gairik, and Guduchi Sattva have been titrated in this formulation keeping the above principle in mind. Ideally, after experimentation, it is found that for optimum effect of MKD the composition should contain equal amounts (12 wt % each) of Mouktik Bhasma, Praval Bhasma, Shankha Bhasma. Shouktik Bhasma, Kapardik Bhasma, Shudhha Gairik and Guduchi Sattva, which are bound together with a natural gum such as gum acacia to the extent of 16 wt %. The ingredients in powder form are blended together. The natural gum is added to the powder blend to form dough along with purified water. Pellets are formed from this dough having average of 5 gm. These pellets are tray dried typically at temperature in the range of 40-45° C. The dried pellets are granulated in a mixer grinder and the dry granules are taken for compression tableting. The average weight of the uncoated tablets is 300 mg±5%. The typical shelf life of these tablets is 3 years.

Shankha bhasma is prepared from conch shell.
Shouktik bhasma is prepared from pearl shell.
Kapardika Bhasma is prepared from Cowries.
Pravala Bhasma is prepared from Coral.
Mouktik bhasma is prepared from pearl.
Guduchi Sattva is obtained from *Tinospora* plant species. The *Tinospora* is selected from *Tinospora cordifolia*, and *Tinospora* sinensis.

*Tinospora cordifolia* is also known as Guduchi of the family Menispermaceae. *Tinospora cordifolia* is indigenous to the tropical areas of India, Myanmar, and Sri Lanka. It is obtained from Bharatiya Sanskriti Darshan Trust (BSDT), Wagholi, Pune.

*Tinospora sinensis* is also known as Malabar Gulbel or Gulvel of the family Menispermaceae. *Tinospora sinensis* is found in India, China, Sri Lanka, Nepal, Cambodia, Thailand, Vietnam, and Myanmar. It is obtained from Bharatiya Sanskriti Darshan Trust (BSDT), Wagholi, Pune.

In one embodiment, the MKD comprises equal quantities of Mouktik bhasma, Shankha bhasma, Shouktik bhasma, Kapardik bhasma, Praval bhasma, Guduchi sattva, Shudhha Gairik, and at least one excipient, typically a natural gum, in an amount ranging from 10 wt % to 30 wt % of the total weight of the MKD.

Shuddha Gairik is a natural clay earth pigment which is a mixture of ferric oxide and varying amounts of clay and sand.

In an embodiment of the present disclosure, the excipient is selected from the group consisting of gum acacia, guar gum, and xanthan gum.

The MKD is administered at a dose of 800 mg to 1200 mg per day by oral administration.

Praval Pishti Vati (PPV) comprises coral powder passed through mesh number 200 having particle size in the range of 50 microns to 75 microns triturated in rose water and dried to obtain Praval Pishti, wherein the total amount of dried triturated coral powder is in the range of 75 wt % to 92 wt % of the total weight of the Praval Pishti Vati, and at least one excipient in an amount ranging from 8 wt % to 25 wt % of the total weight of the Praval Pishti Vati.

Praval Pishti powder is mixed with natural gum and purified water to form dough. Pellets are formed from this dough. These pellets are tray dried typically at a temperature in the range of 40-45° C. The dried pellets are granulated in a mixer grinder and the dry granules are taken for compression tableting. The average weight of the uncoated tablets is 300 mg±5%. The typical shelf life of these tablets is 3 years.

Praval Pishti Vati is obtained from Bharatiya Sanskriti Darshan Trust (BSDT), Wagholi, Pune. The Praval Pishti Vati is administered at a dose of 800 mg to 1200 mg per day by oral route.

The Ananta Vati comprises powder obtained from dried roots of Ananta in an amount ranging from 75 wt % to 92 wt % of the total weight of the Ananta Vati, and at least one excipient in an amount ranging from 8 wt % to 25 wt % of the total weight of the Ananta Vati. The particle size of the dried root powder is in the range of 150 microns to 180 microns.

The excipient is a binder. The binder is at least one selected from the group consisting of gum acacia, guar gum, and xanthan gum. In an exemplary embodiment, the binder is gum acacia.

In an embodiment, the Ananta vati comprises powder obtained from roots of *Decalepis hamiltonii* in an amount ranging from 75 wt % to 92 wt % of the total weight of the Ananta vati, and at least one excipient in an amount ranging from 8 wt % to 25 wt % of the total weight of the Ananta vati. In another embodiment other species related to Ananta such *Hemidesmus indicus, Cryptolepis buchnani, Ichnocarpus frutescens* and the like can also be used in the herbo-mineral composition of the present disclosure.

Ananta powder is mixed with natural gum to form dough along with purified water. Pellets are formed from this dough. These pellets are tray dried typically at a temperature in the range of 40-45° C. The dried pellets are granulated in a mixer grinder and the dry granules are taken for compression tableting. The average weight of the uncoated tablets is 300 mg±5%. The typical shelf life of these tablets is 3 years.

Ananta is selected from *Decalepis hamiltonii* and is obtained from Bharatiya Sanskriti Darshan Trust (BSDT), Wagholi, Pune. The Ananta vati is administered at a dose of 1.8 gm to 2.2 gm per day by oral route.

The compositions of MKD, PPV, and Ananta Vati are prepared in a solid dosage form selected from the group consisting of tablet, pill, and capsule.

A combination of Padmakadi Ghrut (PDG), Mouktikyukta Kamdudha Vati (MKD), Praval Pishti Vati (PPV), and Ananta Vati in the kit is used for minimizing the adverse effects of chemotherapy and improving the quality of life.

The rationale for selecting the individual components of the kit and their compositions are as follows:

PDG is a novel proprietary medicine in the form of medicated ghee. It is prepared by adding fresh juice of petals and stalks of Padmak flowers (*Nelumbo nucifera*), whole plant of Durva (*Cynodon dactylon*), and decoction of roots of Ananta from the plant which is at least one selected from the group consisting of *Decalepis hamiltonii, Hemidesmus indicus, Cryptolepis buchnani*, and *Ichnocarpus frutescens*.

Padmak flowers produce cooling effect, immunomodulatory effect, detoxifying effect and an anti-inflammatory effect. Due to its cooling effect, it eliminates excessive heat in blood and pacifies acidity. The chemotherapy induced adverse effects like burning sensation all over body, fever, and skin discolouration are reduced with aqueous extract of Padmak flowers processed in ghee obtained from cow's milk.

Durva (*Cynodon dactylon*) mainly imparts its cooling effect on gastrointestinal (GI) system. Thus, it is beneficial to control chemotherapy induced loss of taste and vomiting by pacifying acidity.

Ananta (*Decalepis hamiltonii*) also imparts similar properties as that of Durva. It additionally improves appetite, detoxifies blood, and controls fever.

Cow's ghee used for preparing clarified medicated butter itself has independent medicinal properties. It improves appetite, increases strength, eliminates toxins and excessive heat, and heals ulcers. All these properties of ghee reduce adverse effects due to chemotherapeutic drugs.

Overall, PDG in its unique combination, assists in minimizing the side effects of chemotherapy by rectifying the disorders of gastro-intestinal system, detoxifying blood, reducing inflammation and imparting hepato-protection. Cow's ghee in PDG holds the components of PDG together and improves their mode of action synergistically.

Mouktikyukta Kamdudha (MKD) is a herbo-mineral medicine containing Guduchi (*Tinospora cordifolia*) sattva as a herbal content and Shankh bhasma (Conch shell), Shouktik bhasma (Pearl shell), Kapardik bhasma (Cowries), Praval bhasma (Coral), Mouktik bhasma (Pearl) and Gairik (Red ochre) as mineral contents.

Mouktik Bhasma and Praval Bhasma are minerals which reduce inflammation, imparts-cooling effect on tissues, and promote proper nourishment to tissues. They help to reduce chemotherapy induced stomatitis and loss of weight. Combination of Shankha bhasma, Shouktik bhasma and Kapardik Bhasma improves digestion. Guduchi sattva is rejuvenating, anti-pyretic and immunomodulatory in nature. Shuddha Gairik has cooling and wound-healing properties.

Overall, MKD alleviates lack of taste and vomiting by improving digestion. Nausea and loss of taste developed during course of chemotherapy are well controlled with this combination.

Praval (coral) has rejuvenator effect, anti-pyretic effect and detoxifying effect which is beneficial in chemotherapy induced adverse effects like stomatitis, loss of taste and boosting up immunity. Trituration of Praval in rose water (Praval Pishti) gives additional cooling effect.

Ananta vati has mainly detoxifying effect in the blood. The active components of Ananta in Ananta Vati have an immediate effect in detoxifying the blood whereas the active components of Ananta bound in PDG provide sustained response. These active components are released slowly thus having long lasting immunomodulatory effect and improved anti-oxidant activity.

All these four constituents of the herbo-mineral kit synergistically show cooling, anti-pyretic, anti-emetic, anti-inflammatory properties and improvement in complexion. Additionally, PDG smoothens gastrointestinal tract (GI tract) and improves gross as well as micro level absorption, thus improving metabolism.

Overall, the herbo-mineral kit of the present disclosure alleviates the adverse effects of chemotherapy and improves quality of life.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Example 1: Preparation of the Herbo-Mineral Kit in Accordance with the Present Disclosure A herbo-mineral kit was prepared in accordance with the present disclosure.

The components of the herbo-mineral kit are given in Table-1.

TABLE 1

Components of the herbo-mineral kit containing oral medicines

| Sr. No. | Medicine | Quantity per dose | Time |
|---|---|---|---|
| 1 | Padmakadi Ghrut (PDG) | 5 gm (1 tsp) | Before Lunch & Dinner |
| 2 | Mouktikyukta Kamdudha Vati (MKD) | 500 mg (2 tablets) | Morning-Evening |
| 3 | Praval Pishti Vati (PPV) | 500 mg (2 tablets) | Morning-Evening |
| 4 | Ananta Vati | 1 gm (4 tablets) | After Lunch & Dinner |

Experiment 1: Composition of PDG in Accordance with the Present Disclosure

TABLE 2

Composition of Padmakadi ghrut (PDG)

| Sr. No. | Contents | Common Name | Quantity of ingredients to prepare 10 kg of finished product-Batch 1 | Quantity of ingredients to prepare 10 kg of finished product-Batch 2 | Quantity of ingredients to prepare 10 kg of finished product-Batch 3 |
|---|---|---|---|---|---|
| 1 | An aqueous extract of *Nelumbo nucifera* | Padmaka | 5.6 L | 2.5 L | 7.5 L |
| 2 | An aqueous extract of *Cynodon dactylon* | Durva | 5.6 L | 2.5 L | 7.5 L |
| 3 | Decoction of *Decalepis hamiltonii* | Ananta | 5.6 L | 2.5 L | 7.5 L |
| 4 | Clarified butter | Ghruta, Ghrita, Cow's ghee | 10 Kg | 10 Kg | 10 Kg |

Padmakadi Ghrut (PDG) was prepared using the ingredients as given in Table-2 using following process:

Process for Preparing Padmakadi Ghrut (PDG)

Step I: Preparation of Extract of Petals and Stalks of Flower of Padmak (*Nelumbo nucifera*)

3.3 Kg of petals and stalks of flowers of Padmak (*Nelumbo nucifera*) were obtained. The petals and stalks of flower of *Nelumbo nucifera* were chopped in pieces wherein the petal to stalk ratio was 3:1 and mixed with (4.2 L) water to have the petals and stalks of *Nelumbo nucifera* to water ratio as 1:1.25. The chopped pieces of petal and stalks of flowers of *Nelumbo nucifera* and water were grinded in a mixer grinder and filtered through a muslin cloth to obtain an aqueous extract of petals and stalks of flowers of *Nelumbo nucifera*, which was used in the preparation of the herbal composition.

Step II: Preparation of Extract of Whole Durva Plant (*Cynodon dactylon*)

Separately, 3.3 Kg of whole plant of *Cynodon dactylon* was obtained and chopped into pieces. The chopped Durva plants were grinded by adding 6 L water to obtain a blend, wherein the ratio of *Cynodon dactylon* to water was 1:2. The blend was filtered to obtain a filtrate containing extract of Durva which was used in the preparation of the herbal composition.

Step III: Preparation of Decoction of Roots of Ananta (*Decalepis hamiltonii*)

Further, 3.3 Kg of dried roots of Ananta (*Decalepis hamiltonii*) were obtained and grinded to obtain coarse powder. It was subjected to decoction, wherein the ratio of *Decalepis hamiltonii* root to water was 1:8 and reduced to $¼^{th}$ to obtain decoction of *Decalepis hamiltonii*, which was used in the preparation of herbal composition.

Preparation of PDG

The aqueous extract of petals and stalks of *Nelumbo nucifera* (obtained in the step I), aqueous extract of whole plant of *Cynodon dactylon* (obtained in step II), decoction of roots of *Decalepis hamiltonii* (obtained in step III), and 10 Kg of clarified butter from cow's milk were mixed in a proportion given in Table 2 to obtain a mixture. The mixture was heated uniformly at 100° C. for 60 minutes to evaporate water completely to obtain 10 kg of PDG.

Specification of Padmakadi Ghrut (PDG):
  Description: Greenish semi-solid granular (mass) paste
  Specific gravity at 25° C.: 0.9040 to 0.9140
  Refractive index at 25° C.: 1.535 to 1.545
  Acid value: 1.3500 to 1.7500
  Saponification value: 300 to 370
  Unsaponifiable matter: 0.5 to 4
  Iodine value: 25 to 45
  Peroxide value: 0.5 to 1.5
  Congealing point: 27 to 31
  RM (Reichert-Meissel) value: 5 to 50
  Moisture content: 0 to 0.5%

Experiment 2: Composition of MKD in Accordance with the Present Disclosure

TABLE 3

Composition of MKD

| Sr. No. | Contents | Latin name/English Name | Quantity for 30 kg of finished product-Batch 1 | Quantity for 30 kg of finished product-Batch 2 | Quantity for 30 kg of finished product-Batch 3 |
| --- | --- | --- | --- | --- | --- |
| 1 | Mouktik Bhasma | Incinerated Pearl | 3572 g | 3500 | 4000 |
| 2 | Shankha Bhasma | Incinerated Conch | 3572 g | 3000 | 3800 |
| 3 | Shouktik Bhasma | Incinerated Pearl Shell | 3572 g | 3000 | 3800 |
| 4 | Kapardik Bhasma | Incinerated Cowrie | 3572 g | 3000 | 3800 |
| 5 | Praval Bhasma | Incinerated Coral | 3572 g | 3500 | 3800 |
| 6 | An aqueous extract of *Tinospora cordifolia/sinensis* | Starch of *Tinospora cordifolia/sinensis* | 3572 g | 3500 | 4000 |
| 7 | Shuddha Gairik | Red ochre roasted in cow ghee | 3572 g | 3000 | 3800 |
| 8 | Gum Acacia powder | | 5000 g | 7500 | 3000 |

MKD was prepared using the ingredients as given in Table-3, by following process:

Process for Preparing Mouktikyukta Kamdudha Vati (MKD)

Mouktik bhasma, Shankha bhasma, Shouktik bhasma, Kapardik bhasma, Praval bhasma (all these five bhasma are prepared using textual methods), Guduchi Sattva (starch of *Tinospora cordifolia/sinensis*), Gairik and gum acacia powder were mixed in a proportion given in Table 3. To this mixture, sufficient amount of water was added to obtain a dough. The dough was further pelletized to obtain pellets. The so obtained pellets were dried in oven at 45° C. to obtain dried pellets. The dried pellets were grinded to obtain granules having powder to granule ratio of 30:70. The mixture of granules and powder was compressed in tablet punching machine to obtain compressed tablet each having weight 300 mg±5%.

Specification of Shankha Bhasma:
   Description—Greyish white very fine powder
   Loss on drying—NMT 1% w/w
   Acid insoluble ash—NMT 2% w/w
   pH—9 to 10
   Calcium assay as Ca—38 to 40% w/w Specification of Shouktik Bhasma:
   Description—Greyish white very fine powder
   Loss on drying—NMT 1% w/w
   Acid insoluble ash—NMT 2% w/w
   pH—10 to 11
   Calcium assay as Ca—38 to 40% w/w Specification of Kapardik Bhasma:
   Description—Greyish white very fine powder
   Loss on drying—NMT 1% w/w
   Acid insoluble ash—NMT 2% w/w
   pH—10 to 11
   Calcium assay as Ca 38 to 40% w/w Specification of Praval Bhasma:
   Description—Greyish white very fine powder
   Loss on drying—NMT 1% w/w
   Acid insoluble ash—NMT 2% w/w
   pH—10 to 11
   Calcium assay as Ca—40 to 45% w/w Specification of Mouktik (Pearl) Bhasma:
   Description—Greyish white very fine powder
   Loss on drying—NMT 1% w/w
   Acid insoluble ash—NMT 2% w/w
   pH—10 to 11
   Calcium assay as Ca—38 to 40% w/w Specification of Gairik (Red Ochre):
   Loss on drying—NMT 1% w/w
   Iron assay—NLT 15% w/w
   Silica assay—18 to 20% w/w
   Oil content—3 to 3.5% w/w Specification of Guduchi Sattva (Starch of *Tinospora cordifolia/Sinensis*):
   Loss on drying—4 to 5% w/w
   Acid Insoluble ash—NMT 1% w/w
   Gelation temperature—60 to 75° C.

Specification of MKD:
   Description: Light brown colour
   Shape: Round biconvex tablet
   Weight variation: 0.2850 to 0.3150
   Average weight: 0.300
   Hardness: 2 to 4 Kg/cm$^2$
   Friability: NMT 1% w/w
   Disintegration Time: NMT 30 min
   Diameter: 7 to 8 mm
   Width: 3 to 4 mm
   Acute Toxicity: LD 50>2000 mg/kg Experiment 3: Composition of Praval Pishti Vati in Accordance with the Present Disclosure

TABLE 4

| | | | Composition of Praval Pishti Vati | | |
|---|---|---|---|---|---|
| Sr. No. | Contents | Common Name | Quantity for 15 kg of finished product-Batch 1 | Quantity for 15 kg of finished product-Batch 2 | Quantity for 15 kg of finished product-Batch 3 |
| 1 | Powder of Praval triturated in rose water | Praval Pishti | 12000 g | 11250 g | 13500 g |
| 2 | Gum Acacia powder | | 3000 g | 3750 g | 1500 g |

Praval Pishti Vati was prepared using the ingredients as given in Table-4, by the following process:

Process for Preparing Praval Pishti Vati:

12600 μm of dried Praval was powdered in pulveriser and sifted through sieve no. 200 to get 12000 μm praval powder. It was then triturated with 24000 ml of rose water for 7 times and dried to evaporate water completely to obtain Praval Pishti. In a mass mixer, powders of 12000 gm of Praval Pishti and 3000 gms gum acacia were mixed in a proportion given in Table 4. To this mixture, water was added to obtain a dough. The dough was further pelletized to obtain pellets. The pellets were dried in oven at 45° C. to obtain dried pellets. The dried pellets were grinded to obtain granules having powder to granule ratio of 30:70. The granules and powder were compressed in tablet punching machine to obtain compressed tablets each of weight 300 mg±5%.

Specification of Praval Pishti Vati:
   Description: Light Pink colour
   Shape: Round biconvex tablets
   Weight variation: 0.2850 to 0.3150
   Average weight: 0.3000
   Hardness: 1 to 4 Kg/cm$^2$
   Friability: NMT 1% w/w
   Disintegration Time: NMT 15 min
   Diameter: 8 to 9 mm
   Width: 3 to 4 mm Experiment 4: Composition of Ananta Vati in Accordance with the Present Disclosure

TABLE 5

| | | | Composition of Ananta Vati | | |
|---|---|---|---|---|---|
| Sr. No. | Contents | Common Name | Quantity for 30 kg of finished product-Batch 1 | Quantity for 30 kg of finished product-Batch 2 | Quantity for 30 kg of finished product-Batch 3 |
| 1 | Powder of *Decalepis hamiltonii* | Ananta | 25000 g | 22500 | 27500 |
| 2 | Gum Acacia powder | | 5000 g | 7500 | 2500 |

Ananta Vati was prepared using the ingredients as given in Table-5, by using the following process:

Process for Preparing Ananta Vati

In a mass mixer, 25000 μm of powder of dried root of *Decalepis hamiltonii* and 5000 μm of gum acacia were mixed in a proportion given in Table 5. To this mixture, water was added to obtain a dough. The dough was further pelletized to obtain pellets. The pellets were dried in oven at 45° C. to obtain dried pellets. The dried pellets were grinded to obtain granules having powder to granule ratio of 30:70. The granules and powder were compressed in tablet punching machine to obtain compressed tablets each of weight 300 mg±5%.

Specification of Ananta Vati:
  Description: Light brown colour
  Shape: Round biconvex tablets
  Weight variation: 0.2850 to 0.3150
  Average weight: 0.300
  Hardness: 1 to 4 Kg/cm$^2$
  Friability: NMT 1% w/w
  Disintegration Time: NMT 15 min
  Diameter: 10 to 11 mm
  Width: 4 to 5 mm Example 2

Efficacy Studies of the Herbo-Mineral Kit of the Present Disclosure Compared to Absolute Control Group (Control Group 1) with No Herbo-Mineral Treatment During Chemotherapy in Breast Cancer Patients The present herbo-mineral kit contains PDG, MKD, PPV, and Ananta Vati which has effect of alleviating adverse effects of chemotherapy. These, 4 components of the present disclosure have a synergistic effect in reducing the toxic side effects of chemotherapy and improving quality of life. To study this, two groups of breast cancer patients receiving the herbo-mineral kit of the present disclosure (Study Group) and absolute control group (Control 1) not receiving herbo-mineral kit were compared for chemotherapy induced side effects and quality of life.

In this study, 26 breast cancer patients, treated with surgery, scheduled for chemotherapy were included. Out of these, 13 patients were given additional herbo-mineral kit of the present disclosure mentioned hereinabove (Study Group) while 13 patients received only chemotherapy (Control 1 group). The stage and grade of the disease were matched for both the groups. Treatment for Study Group was given from start of chemotherapy till completion of chemotherapy of individual patient.

Inclusion Criteria for Enrolling Patients in this Study
  Female patients: Age group between 25-75 years, operated for breast cancer, who were in Stage I, II and III of the disease and were eligible for chemotherapy.
Exclusion Criteria for Enrolling Patients in this Study
  Patients who were on other Ayurvedic drugs for any other ailment and patients with distant metastasis and recurrence.
Outcome Measures—Time Points for Assessment of Outcome Measures—
  A—Before chemotherapy for clinical investigations and quality of life while for symptoms of adverse effects 1 week after 1$^{st}$ cycle of chemotherapy.
  B—End of Chemotherapy.
A. Clinical Investigations
  The patients were followed up for:
  Assessment of adverse effects clinically and graded using CTCAE 4.03 Version (Grading of symptoms on 0 to 4 scale). Lower scale denotes less severity of the symptoms.
  Assessment of performance status using Karnofsky score (Grading for well-being on 0 to 100 scale, higher score denotes better performance).
  Assessment of Quality of Life (QoL) using Questionnaire QLQ C30 (designed for all types of cancers) of European Organization for Research and Treatment of Cancer (EORTC) determined on the basis of patients' own perspective about own well-being.
  QLQ C30 can be interpreted as—
  1. Symptomatology (Symptom score)
  2. Ability to perform routine activities (Functional score)
  3. Overall well-being (Global score)
  Karnofsky score and scoring for QoL are internationally accepted means of scoring symptoms and quality of life for cancer patients used in various studies in clinical trials.
  The data was analyzed as fold increase/decrease in a given parameter compared to its level at time point A. For symptoms Mann Whitney Z test and for scores paired T test were applied.

Experiment 1: Alleviation of Adverse Effects of Chemotherapy in Breast Cancer Patients Using Herbo-Mineral Kit of the Present Disclosure and Absolute Control (Control 1) without any Herbo-Mineral Kit Out of commonly observed adverse effects, 7 significant symptoms were recorded in this study on the scale of grade 0-4. The mean of gradation at both the time points was recorded for both the groups. The observations for each group at time point B were compared with respective time point A (After 1 cycle of chemotherapy, since chemotherapy induced adverse effects show up after chemotherapy starts) and fold change histograms were plotted.

Results:

Nausea and Vomiting—Both the groups show increase in nausea and vomiting during the period of chemotherapy (time points—A to B). However, the Study Group shows significant (p=0.0961) while highly significant (p=0.0092) decrease in nausea and vomiting, respectively, compared to their respective Control 1 at time point B. (FIG. 1).

Constipation—Both the groups show increase in constipation at time point B as compared to their respective time point A. However, they do not show significant difference (FIG. 1).

Stomatitis—It is interesting to note that study Group does not reveal any symptom of stomatitis at time point B (FIG. 1). While control 1 Group shows decrease in gradation of stomatitis at time point B as compared to its time point A.

Figure 2:
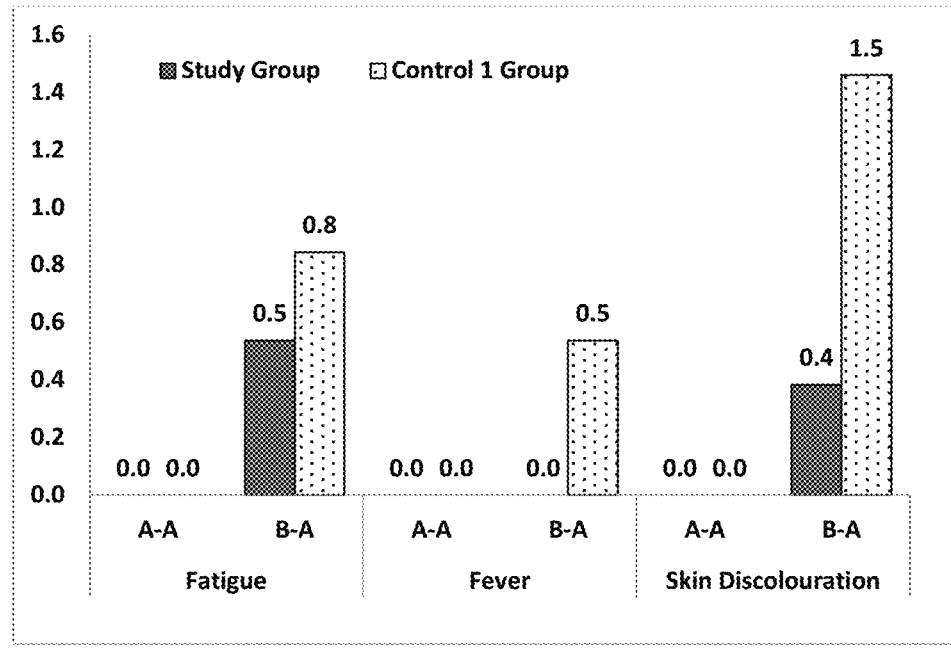
FIG. 2 depicts a graphical representation of the effect of the herbo-mineral kit treatment on chemotherapy induced fatigue, fever and skin discoloration in study and control 1 group patients.

Fatigue and Fever—Control 1 Group shows increase in fatigue as well as fever at time point B as compared to its respective time point A. However, Study Group shows increase in case of fatigue while no fever was recorded at time point B. Moreover, the decrease in fever for the Study Group is highly significant (p=0.001) as compared to Control 1 Group at time point B (FIG. 2).

Skin discoloration—Both the groups show increase in skin discoloration at time point B as compared to their respective time point A. However, the Study Group shows very highly significant (p=0.0008) decrease in discoloration as compared to Control 1 Group (FIG. 2).

Figure 3:
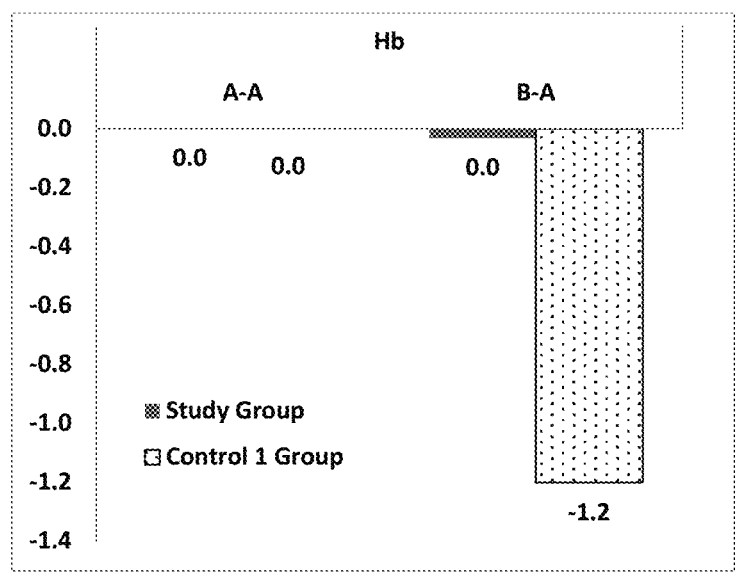
FIG. 3 depicts a graphical representation of the effect of the herbo-mineral kit treatment on Haemoglobin in study and control 1 group patients.
Figure 4:
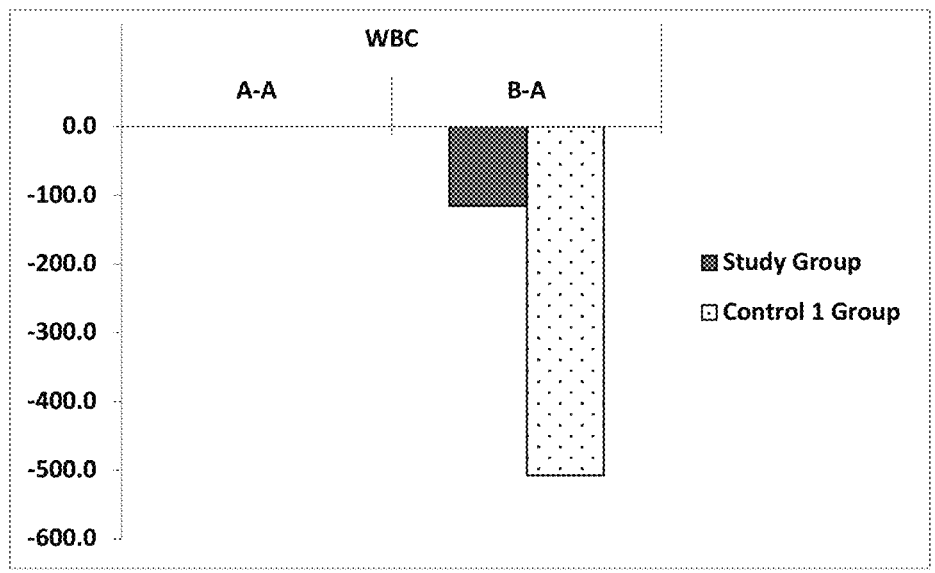
FIG. 4 depicts a graphical representation of the effect of the herbo-mineral kit treatment on WBC count in study and control 1 group patients.
Figure 5:
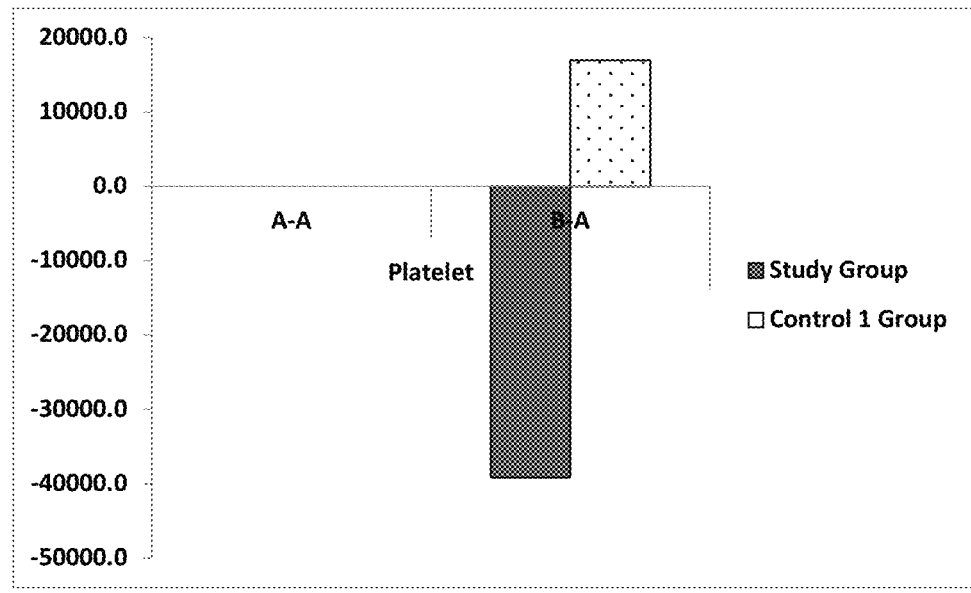
FIG. 5 depicts a graphical representation of the effect of the herbo-mineral kit treatment on Platelet count in study and control 1 group patients.

Experiment 2: Assessment of Haemogram and Other Biochemical Parameters in Breast Cancer Patients Using Herbo-Mineral Kit of the Present Disclosure and Absolute Control (Control 1) without any Herbo-Mineral Kit Results:

Haemoglobin, WBC and Platelets show reduced values in both the groups but are within the normal range. The change is more pronounced in Study Group compared to their respective Control 1 Group (FIGS. 3, 4 and 5).

Figure 6:
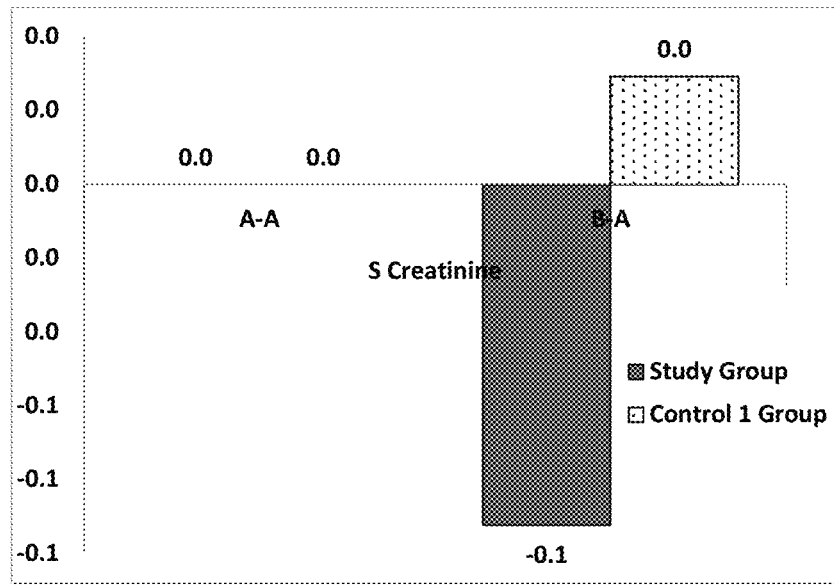
FIG. 6 depicts a graphical representation of the effect of the herbo-mineral kit treatment on Serum Creatinine in study and control 1 group patients.

Liver function tests such as S. Bilirubin, SGOT, SGPT, and alkaline phosphatase do not show variation in both the groups, hence the figures are not included in the present disclosure. Serum creatinine shows significant decrease in the Study Group as compared to the Control 1 Group at time point B, although within the normal range (FIG. 6).

Figure 7:
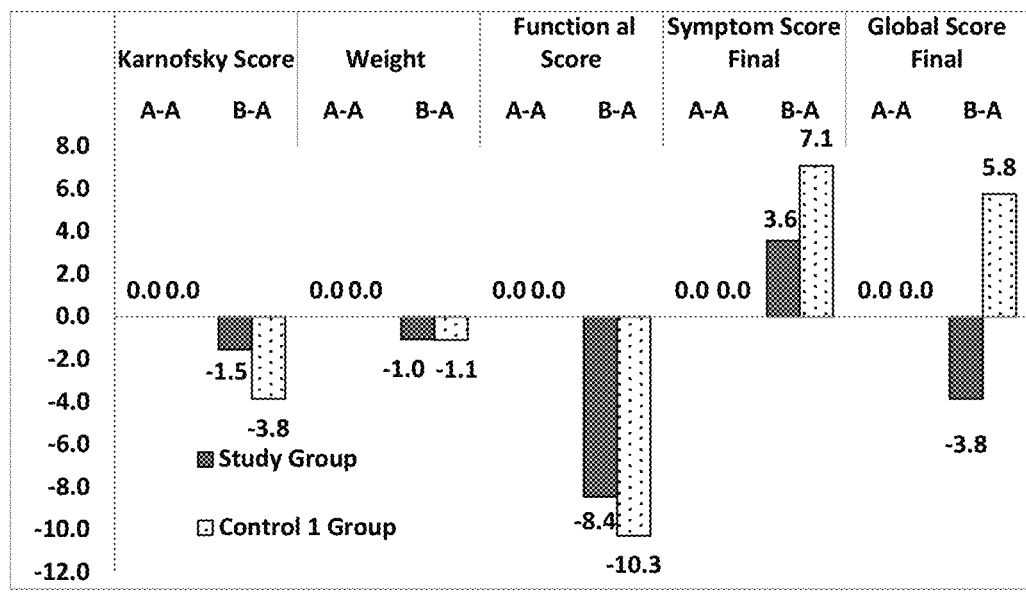
FIG. 7 depicts a graphical representation of the effect of the herbo-mineral kit treatment on Karnofsky score, weight, Functional score, Symptom score and Global score in study and control 1 group patients.

Experiment 3: Assessment of Quality of Life in Breast Cancer Patients Using Herbo-Mineral Kit of the Present Disclosure and Absolute Control (Control 1) without any Herbo-Mineral Kit Results:

Karnofsky score, weight and Functional score: All the three parameters show decrease in both the groups at time point B compared to respective time point A. However, Karnofsky and Functional score of the Study Group show better outcome as compared to Control 1 Group whereas both the groups reveal no change in the weight (FIG. 7).

Symptom score: Both the Groups show higher score at time point B as compared to respective time point A. However, the Study Group reveals larger decrease in symptoms as compared to Control 1 Group (FIG. 7).

Global score: The Global score of Control 1 Group shows better outcome as compared to that of the Study Group at time point B although the difference is not statistically significant (FIG. 7).

The example 2 was to assess performance of herbo-mineral kit of present disclosure with that of absolute Control 1 group. Overall, it is evident that the herbo-mineral kit of present disclosure shows significantly better outcome with respect to alleviation of adverse symptoms such as nausea, vomiting, fever and skin discoloration caused due to chemotherapy in breast cancer patients as compared to absolute control. In case of adverse symptoms such as constipation, stomatitis, and fatigue the outcome is better although not significant with the treatment of herbo-mineral kit as compared to absolute control. As for quality of life it remained steady for both the groups with slight better outcome for the Study Group. It is quite evident that the components of the herbo-mineral kit of present disclosure have synergistic effect on the control of adverse effects of chemotherapy in the patients treated with chemotherapy.

Example 3

Efficacy Studies of the Herbo-Mineral Kit of the Present Disclosure Compared to Control Group (Control Group 2) Treated with Herbo-Mineral Components Shatavari Kalpa, MKD, PPV, and Ananta Vati During Chemotherapy in Breast Cancer Patients In this study, the present herbo-mineral kit containing PDG, MKD, PPV and Ananta Vati has been compared with a herbo-mineral composition containing Shatavari Kalpa, MKD, PPV and Ananta Vati to study the alleviation of adverse effects of chemotherapy. To study this, two groups of breast cancer patients, one receiving the herbo-mineral kit of the present disclosure (Study Group) and second receiving herbo-mineral composition containing Shatavari Kalpa, MKD, PPV and Ananta Vati (Control 2 Group) were compared for chemotherapy induced side effects and quality of life.

The study compiled here is a retrospective analysis of patients treated with present disclosure for management of toxic side-effects of chemotherapeutic drugs. In this study, 38 breast cancer patients, treated with surgery, scheduled for chemotherapy were included. Out of these, 18 patients were given herbo-mineral kit of the present disclosure (Study Group) while 20 patients received herbo-mineral composition containing Shatavari Kalpa, MKD, PPV and Ananta Vati (Control 2 group). The stage and grade of the disease were matched for both the groups. Treatment for both the groups was given from start of chemotherapy till completion of chemotherapy of individual patient.

Inclusion Criteria for Enrolling Patients in this Study

Female patients: Age group between 25-75 years, operated for breast cancer, which were in Stage I, II and III of the disease and were eligible for chemotherapy.

Exclusion Criteria for Enrolling Patients in this Study

Patients who were on other Ayurvedic drugs for any other ailment and patients with distant metastasis and recurrence.

TABLE 6

Stage of patients included in the study

| Stage | Study group (n = 18) | Control group (n = 20) |
|---|---|---|
| I-II | 10 | 11 |
| III | 8 | 09 |
| Total | 18 | 20 |

It can be seen from the table that the stage-wise distribution of patients in the study group and control group are comparable.

Outcome measures—Outcome measures were assessed after completion of chemotherapy and across group comparison was performed for each criterion.

Clinical Investigations for symptoms and Karnofsky score of the enrolled patients: The patients were followed up for—

Clinical assessment of adverse effects using gradation based on CTCAE 4.03 Version (Grading of symptoms on 0 to 4 scales, lower scales denote less severity of the symptoms).

Since chemotherapy induced side effects are visible only after starting chemotherapy and increased as the chemotherapy progresses, comparison has been made between the grade of symptoms in study group and control 2 group at the end of chemotherapy (B).

Quality of life was assessed using Karnofsky score (Grading for well-being on 0 to 100 scales, higher score denotes better performance) and weight. Karnofsky score is internationally accepted scoring system by the physician. The data was analyzed as fold increase/decrease in these two parameters compared to its level before chemotherapy (A) and after completion of chemotherapy (B). For symptoms Mann Whitney Z test and for scores paired 't' test were applied.

Figure 8:
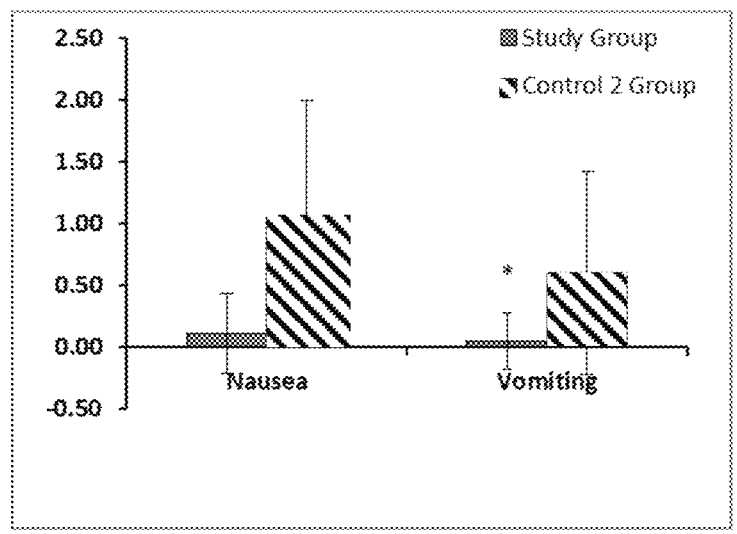
FIG. 8 depicts a graphical representation of the effect of the herbo-mineral kit treatment on chemotherapy induced nausea and vomiting in study and control 2 group patients.

Experiment 1: Alleviation of Adverse Effects of Chemotherapy and Karnofsky Score in Breast Cancer Patients Using Herbo-Mineral Kit of the Present Disclosure and Control Group (Control 2 Group) Treated with Herbo-Mineral Components Shatavari Kalpa, MKD, PPV, and Ananta Vati Results:

Nausea and Vomiting—The Study Group shows less nausea and vomiting as compared to the Control 2 Group wherein the decrease in nausea is very highly significant (p=0.0003) and vomiting is significant (p=0.0102) as assessed at the end of chemotherapy (FIG. 8).

Figure 9:
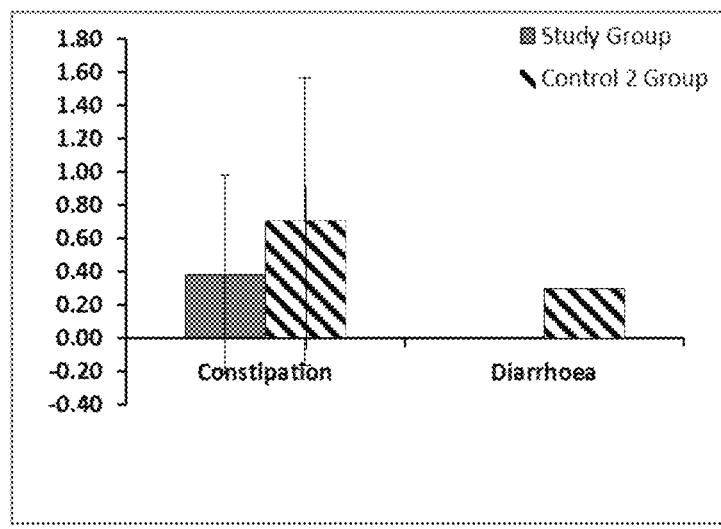
FIG. 9 depicts a graphical representation of the effect of the herbo-mineral kit treatment on chemotherapy induced constipation and diarrhea in study and control 2 group patients.

Constipation and Diarrhoea—The Study Group shows less constipation and diarrhea as compared to Control 2 Group at the end of chemotherapy (FIG. 9).

Figure 10:
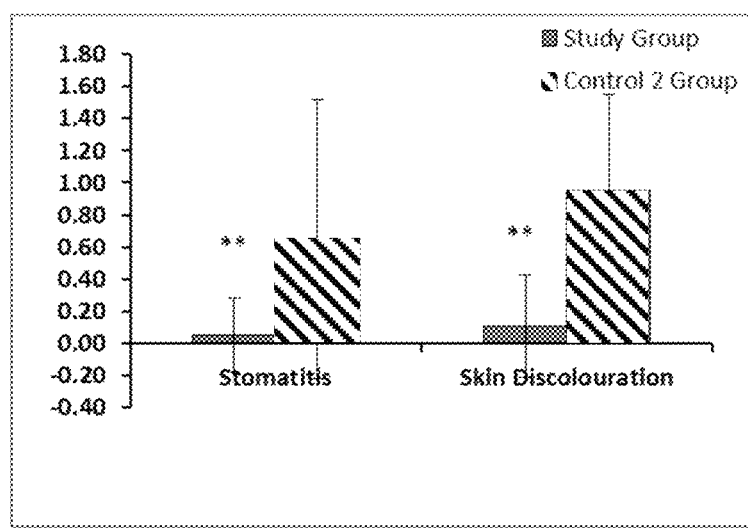
FIG. 10 depicts a graphical representation of the effect of the herbo-mineral kit treatment on chemotherapy induced stomatitis and skin discoloration in study and control 2 group patients.

Stomatitis and Skin Discoloration—Study Group shows highly significant (p=0.0084 and p=0.0001, respectively) reduction in stomatitis and skin discoloration as compared to Control 2 Group (FIG. 10).

Figure 11:
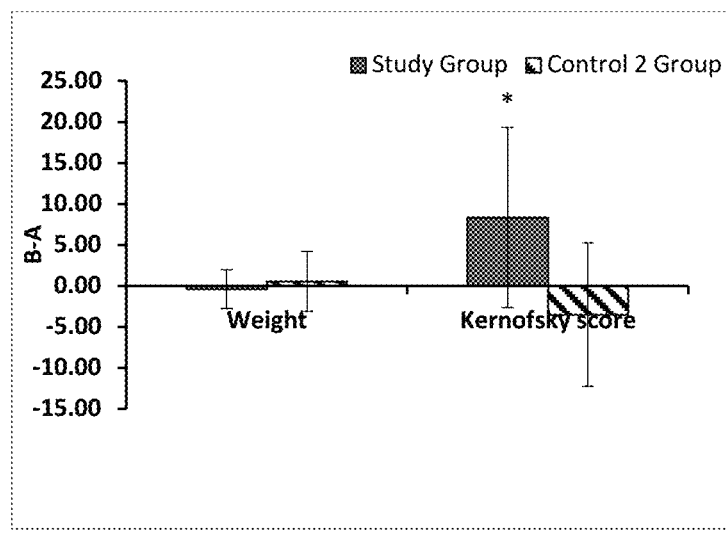
FIG. 11 depicts a graphical representation of the effect of the herbo-mineral kit treatment on weight and Karnofsky score in study and control 2 group patients at the end of chemotherapy.

Weight and Karnofsky score: There is no change in the weight of the patients in both the groups while Karnofsky score denotes significantly higher value (p=0.0025) in the Study Group as compared to the Control 2 Group (FIG. 11).

The example 3 was to assess performance of herbo-mineral composition of present disclosure with that of Control 2 group treated with herbo-mineral components Shatavari Kalpa, MKD, PPV, and Ananta Vati. In this example, the effect of Padmakadi Ghrut was compared with Shatavari Kalpa, rest of the components being identical in both the groups. Shatavari is a commonly used Rasayana having properties such as strengthening, cooling, and immunomodulatory either used singly or in combinations in many diseases. The present disclosure containing Padmakadi Ghrut shows significantly better outcome with respect to alleviation of adverse symptoms such as nausea, vomiting, fever and skin discoloration caused due to chemotherapy in breast cancer patients as compared to combination containing Shatavari. It is also evident that the present disclosure shows better quality of life in terms of Karnofsky score as compared to the composition containing Shatavari.

Overall, the present herbo-mineral kit consisting of PDG, MKD, PPV and Ananta Vati shows better outcomes as compared to the composition containing Shatavari Kalpa, MKD, PPV and Ananta Vati in patients treated with chemotherapy.

Example 4

Case Reports—Two Case Reports of Patients Treated with Herbo-Mineral Kit of the Present Disclosure, Two Case Reports of Patients Treated with Chemotherapy Alone (of Control 1 Group Type) and Two Case Reports of Patients Treated with Herbo-Mineral Components Shatavari Kalpa, MKD, PPV and Ananta Vati (of Control 2 Group Type), Matched for Age, Stage, Grade and ER-PR Status Comparative clinical study of available parameters of 4 controls (2 each of control 1 and control 2 types), and 2 study group patients with comparable stage of the disease is given in Tables 7A and 7B—

TABLE 7A

Demographic and Disease information

| | Stage II | | | Stage IV | | |
|---|---|---|---|---|---|---|
| | Study | Control 1 | Control 2 | Study | Control 1 | Control 2 |
| Age at diagnosis (yrs) | 37 | 49 | 59 | 37 | 57 | 49 |
| Parity | 2 | 2 | 2 | 2 | 5 | 3 |
| Stage | IIB | IIA | IIA | IV | IV | IV |
| Grade | II | III | III | — | I | II |
| Histopathology report | Invasive Ductal Carcinoma | Invasive ductal carcinoma | Infiltrating Ductal Carcinoma | Ductal carcinoma Liver nodule- Metastatic adenocarcinoma | Invasive duct carcinoma | Infiltrating Ductal Carcinoma |

TABLE 7A-continued

Demographic and Disease information

|  | Stage II | | | Stage IV | | |
| --- | --- | --- | --- | --- | --- | --- |
|  | Study | Control 1 | Control 2 | Study | Control 1 | Control 2 |
| ER, PR, Her2 status | ER + ve, PR + ve | ER-Positive-PR/Her2Neu-Neg | ER-ve, PR-ve, Her2 + ve (Score 3) | consistent with known primary As pt was under Tab Tamoxifen for 5 yrs, ER, PR may be positive | ER-Positive-PR/Her2Neu-Neg | ER + ve, PR + ve, Her2-ve |
| Disease status | 1/30 Axillary LN + ve | No nodal metastasis | NA | Liver metastasis | Bone metastasis + ? spleen metastasis | Bone and pulmonary metastasis |
| Conventional treatment taken | Surgery-Breast lumpectomy, MRM, 6 CH cycles FEC Hormonal Rx Tab Tamoxifen for 5 yrs | Surgery-Lt Sector mastectomy done, , 4 AC + 4 Docetaxel chemotherapy + 25 #/50 Gy to chest wall followed by Tab Tamoxifen | Surgery wide excision SLNB + Axillary sampling 3 CH Cycles FEC 12 cycles Paclitaxel + Herceptin Maintenance 12 CH Cycles Inj. Bicertis 440 mg 20 Fractions of RT | 6 CH Cycles CAF Hormonal Rx Tab Tamoxifen 10 mg BD for 5 yrs | 4 AC + 4 Paclitaxel chemotherapy given | 6 CH Cycles CAF Hormonal Rx Tab Tamoxifen 20 mg BD for 5 yrs + Palliative radiotherapy given to spine |
| Duration of additional treatment | 35 wks (with herbo-mineral kit of present disclosure) | 36 wks (composition containing Shatavari Kalpa, MKD, PPV and Ananta Vati) | No treatment | 21 wks (with herbo-mineral kit of present disclosure) | 50 wks (composition containing Shatavari Kalpa, MKD, PPV and Ananta Vati) | No treatment |

MRM-Modified radical mastectomy,
CH-Chemotherapy,
FEC-a combination of three chemotherapy drugs 5 fluorouracil (SFU) + epirubicin + cyclophosphamide,
SLNB-Sentinel lymph node biopsy,
CAF-treatment of Breast Cancer with drugs Cyclophosphamide, Doxorubicin, 5-Fluorouracil,
NA- Information Not Available.

TABLE 7B

Outcome measure results

|  | Stage II patients | | | | | | Stage IV Patients | | | | | |
| --- | --- | --- | --- | --- | --- | --- | --- | --- | --- | --- | --- | --- |
|  | Study | | Control 1 | | Control 2 | | Study | | Control 1 | | Control 2 | |
|  | B. T. | A. T. | B. T. | A. T | B. T. | A. T | B. T. | A. T. | B. T. | A. T. | B. T. | A. T. |
| Clinical parameters | | | | | | | | | | | | |
| Nausea | 1 | 0 | 2 | 2 | 2 | 0 | 0 | 0 | 2 | 0 | 0 | 2 |
| Vomiting | 0 | 0 | 0 | 1 | 0 | 0 | 0 | 0 | 0 | 2 | 0 | 2 |
| Constipation | 2 | 0 | 1 | 0 | 3 | 1 | 2 | 2 | 2 | 2 | 1 | 1 |
| Diarrhea | 0 | 0 | 0 | 0 | 0 | 0 | 0 | 0 | 0 | 0 | 0 | 0 |
| Stomatitis | 1 | 0 | 0 | 1 | 0 | 0 | 3 | 1 | 1 | 1 | 0 | 0 |
| Skin Discoloration | 0 | 0 | 0 | 2 | 2 | 0 | 1 | 0 | 0 | 2 | 0 | 1 |
| Hematological and Biochemical parameters | | | | | | | | | | | | |
| Hb | 12.5 | 13.6 | 13.6 | 11.1 | 13.3 | 12.9 | 11.1 | 11.1 | 11 | 10.1 | 10.2 | 9.2 |
| WBC (In thousand) | 5.9 | 6.2 | 7.1 | 4.5 | 4.1 | 4.9 | 5.1 | 4.1 | 3.2 | 5.8 | 3.2 | 9.2 |
| Platelets (in Lakhs) | NA | 2.14 | 2.96 | 2.39 | 2.17 | 1.56 | 2.78 | 1.96 | 2.32 | 3.31 | 3.32 | 2.54 |
| S. Bilirubin (T) | 0.9 | 0.27 | 0.65 | 0.58 | 0.81 | 0.37 | NA | NA | 1.24 | 1.57 | 0.8 | 0.8 |
| SGOT | 12 | 16.9 | 33 | 62 | 25 | 22.4 | NA | NA | 14 | 27 | 19.5 | 19.8 |
| SGPT | 19 | 17.9 | 27 | 51 | 27 | 22.1 | NA | NA | 16 | 25 | 20.3 | 15 |
| Alkaline phosphatase | 58 | 46.9 | 68 | 77 | 45 | 75.5 | NA | NA | 91 | 100 | 102 | 111 |
| S. Creatinine | 1 | 1.01 | 0.8 | 0.8 | 0.8 | 0.7 | NA | NA | 0.6 | 0.6 | 0.9 | 2.2 |
| Well-being | | | | | | | | | | | | |
| Weight | 70 | 70 | 47.4 | 47.2 | 83 | 79.2 | 64 | 64 | 53.2 | 47 | 74 | 73.5 |
| Karnofsky | 90 | 100 | 90 | 80 | 80 | 80 | 70 | 90 | 90 | 70 | 70 | 50 |
| QoL assessed by QLQ C30 | | | | | | | | | | | | |
| *Symptom score | 31 | 22 | 30 | 40 | 15 | 19 | 14 | 23 | 28 | 38 | 39 | 24 |
| *Functional score | 31 | 25 | 28 | 30 | 13 | 15 | 23 | 39 | 22 | 30 | 40 | 27 |
| *Global score | 8 | 10 | 12 | 8 | 12 | 14 | 6 | 4 | 12 | 7 | 6 | 8 |
| QLQ BR23 score | 21 | 18 | 21 | 34 | 26 | 32 | 44 | 48 | 21 | 30 | 43 | 29 |

TABLE 7B-continued

| | Outcome measure results | | | | | | | | | | | |
|---|---|---|---|---|---|---|---|---|---|---|---|---|
| | Stage II patients | | | | | | Stage IV Patients | | | | | |
| | Study | | Control 1 | | Control 2 | | Study | | Control 1 | | Control 2 | |
| | B. T. | A. T. | B. T. | A. T | B. T. | A. T | B. T. | A. T. | B. T. | A. T. | B. T. | A. T. |
| | | | | | Summary | | | | | | | |
| Favorable response in parameters | 10/12 | | 3/12 | | 8/12 | | 7/12 | | 3/12 | | 5/12 | |
| Stable response in parameters | 1/12 | | 2/12 | | 1/12 | | 2/12 | | 2/12 | | 2/12 | |
| Unfavorable response in parameters | 1/12 | | 7/12 | | 3/12 | | 3/12 | | 7/12 | | 5/12 | |

All hematological and biochemical parameters studied in 3 groups were within normal range. As seen from the summary report of remaining parameters studied, in stage II patient's favorable response and stable response were the highest in study group as compared to both the controls. In case of stage IV patients, favorable response in study group and control 2 group was higher than the control 1 group. Stable response was much better while unfavorable response was much less in the study group as compared to both the control groups. These case reports indicate that the herbo-mineral kit of the present disclosure has more effects in reducing chemotherapy related side effects and therefore improvement in the quality of life of both the patients treated with herbo-mineral kit of the present disclosure.

Overall, it is evident from clinical study depicted in all the examples and case reports that, the herbo-mineral kit of the present disclosure alleviates the adverse effects of chemotherapy in breast cancer patients such as nausea, vomiting, constipation, diarrhea, stomatitis, and skin discolouration. Therefore, the herbo-mineral kit of the present disclosure improves quality of life of cancer patients undergoing chemotherapy.

Technical Advancements

The present disclosure described herein above has several technical advantages including, but not limited to, the realization of a herbo-mineral kit:
that alleviates the symptoms of chemotherapy in cancer such as nausea, vomiting, constipation, diarrhoea, stomatitis, and skin discoloration, and
that improves quality of life of cancer patients undergoing chemotherapy.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveals the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A herbo-mineral kit comprising:
   a first container containing Padmakadi Ghrut (PDG) in a thick, viscous form;
   a second container containing Mouktikyukta Kamdudha Vati (MKD) in a solid dosage form;
   a third container containing Praval Pishti Vati (PPV) in a solid dosage form; and
   a fourth container containing Ananta vati in a solid dosage form.

2. The herbo-mineral kit as claimed in claim 1, wherein said PDG comprises:
   an extract of petals and stalks of Padmak;
   an extract of whole Durva plant;
   a decoction of roots of Ananta; and
   Ghee obtained from cow's milk in an amount ranging from 90 wt % to 98 wt % of the total weight of the PDG,
   wherein said extract of Padmak, said extract of Durva and said decoction of Ananta are independently obtained by using at least one solvent selected from the group consisting of alcohol, water, and a mixture thereof, and wherein the amount of the combined extracts of Padmak, Durva and Ananta is in the range of 2 wt % to 10 wt % of the total weight of the PDG.

3. The herbo-mineral kit as claimed in claim 1, wherein said solid dosage form is selected from the group consisting of tablet, pill and capsule.

4. The herbo-mineral kit as claimed in claim 1, wherein said MKD comprises:
   Mouktik bhasma in an amount ranging from 10 wt % to 14 wt % of the total weight of the MKD;
   Shankha bhasma in an amount ranging from 10 wt % to 14 wt % of the total weight of the MKD;
   Shouktik bhasma in an amount ranging from 10 wt % to 14 wt % of the total weight of the MKD;
   Kapardik bhasma in an amount ranging from 10 wt % to 14 wt % of the total weight of the MKD;
   Praval bhasma in an amount ranging from 10 wt % to 14 wt % of the total weight of the MKD;
   Guduchi sattva in an amount ranging from 10 wt % to 14 wt % of the total weight of the MKD;
   Shudhha Gairik in an amount ranging from 10 wt % to 14 wt % of the total weight of the MKD; and
   at least one excipient in an amount ranging from 2 wt % to 30 wt % of the total weight of the MKD.

5. The herbo-mineral kit as claimed in claim 4, wherein the excipient is a binder.

6. The herbo-mineral kit as claimed in claim 5, wherein said binder is selected from the group consisting of gum acacia, guar gum, xanthan gum and edible gums.

7. The herbo-mineral kit as claimed in claim 1, wherein said Praval Pishti Vati comprises:
   coral powder having a particle size in the range of 50 microns to 75 microns triturated in rose water, wherein the total amount of coral powder and rose water is in the range of 75 wt % to 92 wt % of the total weight of the Praval Pishti Vati; and
   at least one excipient in an amount ranging from 8 wt % to 25 wt % of the total weight of the Praval Pishti Vati.

8. The herbo-mineral kit as claimed in claim 7, wherein the excipient is a binder.

9. The herbo-mineral kit as claimed in claim 8, wherein said binder is selected from the group consisting of gum acacia, guar gum, xanthan gum and edible gums.

10. The herbo-mineral kit as claimed in claim 1, wherein said Ananta vati comprises:
    powder obtained from dried roots of Ananta in an amount ranging from 75 wt % to 92 wt % of the total weight of the Ananta Vati, wherein the powder has a particle size in the range of 150 microns to 180 microns; and
    at least one excipient in an amount ranging from 8 wt % to 25 wt % of the total weight of the Ananta Vati.

11. The herbo-mineral kit as claimed in claim 10, wherein the excipient is a binder.

12. The herbo-mineral kit as claimed in claim 11, wherein said binder is selected from the group consisting of gum acacia, guar gum, xanthan gum and edible gums.

* * * * *